(12) United States Patent
Joshi et al.

(10) Patent No.: US 7,149,417 B2
(45) Date of Patent: Dec. 12, 2006

(54) CONTROLLABLE RELEASE OF A VOLATILE SUBSTANCE

(76) Inventors: Ashok V. Joshi, 4552 S. Thousand Oaks Dr., Salt Lake City, UT (US) 84124; Truman Wold, 823 Greenwood Ter., Salt Lake City, UT (US) 84105

( * ) Notice: Subject to any disclaimer, the term of this patent is extended or adjusted under 35 U.S.C. 154(b) by 0 days.

(21) Appl. No.: 10/708,253

(22) Filed: Feb. 19, 2004

(65) Prior Publication Data
US 2005/0185940 A1    Aug. 25, 2005

(51) Int. Cl.
*F24F 6/00*    (2006.01)
(52) U.S. Cl. .................. 392/390; 392/387
(58) Field of Classification Search ............ 392/386, 392/387, 390, 394, 402, 403; 239/34, 37, 239/38, 42, 43, 53, 54, 55, 56, 57
See application file for complete search history.

(56) References Cited

U.S. PATENT DOCUMENTS

| 2,710,164 | A |   | 6/1955  | Hare |
| 2,991,517 | A |   | 7/1961  | Bundy |
| 3,127,786 | A |   | 4/1964  | Wooley |
| 4,846,003 | A | * | 7/1989  | Marquiss ............... 73/864.24 |
| 4,917,301 | A |   | 4/1990  | Munteanu |
| 4,948,047 | A |   | 8/1990  | Zembrodt |
| 5,810,253 | A | * | 9/1998  | Ohayon .................... 239/43 |
| 5,932,204 | A | * | 8/1999  | Joshi ....................... 424/76.1 |
| 6,109,539 | A |   | 8/2000  | Joshi et al. |
| 6,419,163 | B1|   | 7/2002  | Joshi et al. |
| 6,805,306 | B1| * | 10/2004 | Huang ..................... 239/375 |

OTHER PUBLICATIONS

"International Search Report", (Jan. 19, 2006).

* cited by examiner

*Primary Examiner*—Sang Paik
(74) *Attorney, Agent, or Firm*—David B. Fonda

(57) ABSTRACT

The present invention is directed to a device for releasing a controlled amount of a volatile substance into an environment while isolating the non-released amount of such a substance from the environment. The device includes a housing having an interior region, a volatile substance cartridge associated with the housing, wherein the cartridge can be replaced, or, alternatively, refilled with a desired fluid. A mechanism is provided for releasing a pre-determined amount of fluid from the housing, which is activated, as desired, by a user of the device.

25 Claims, 3 Drawing Sheets

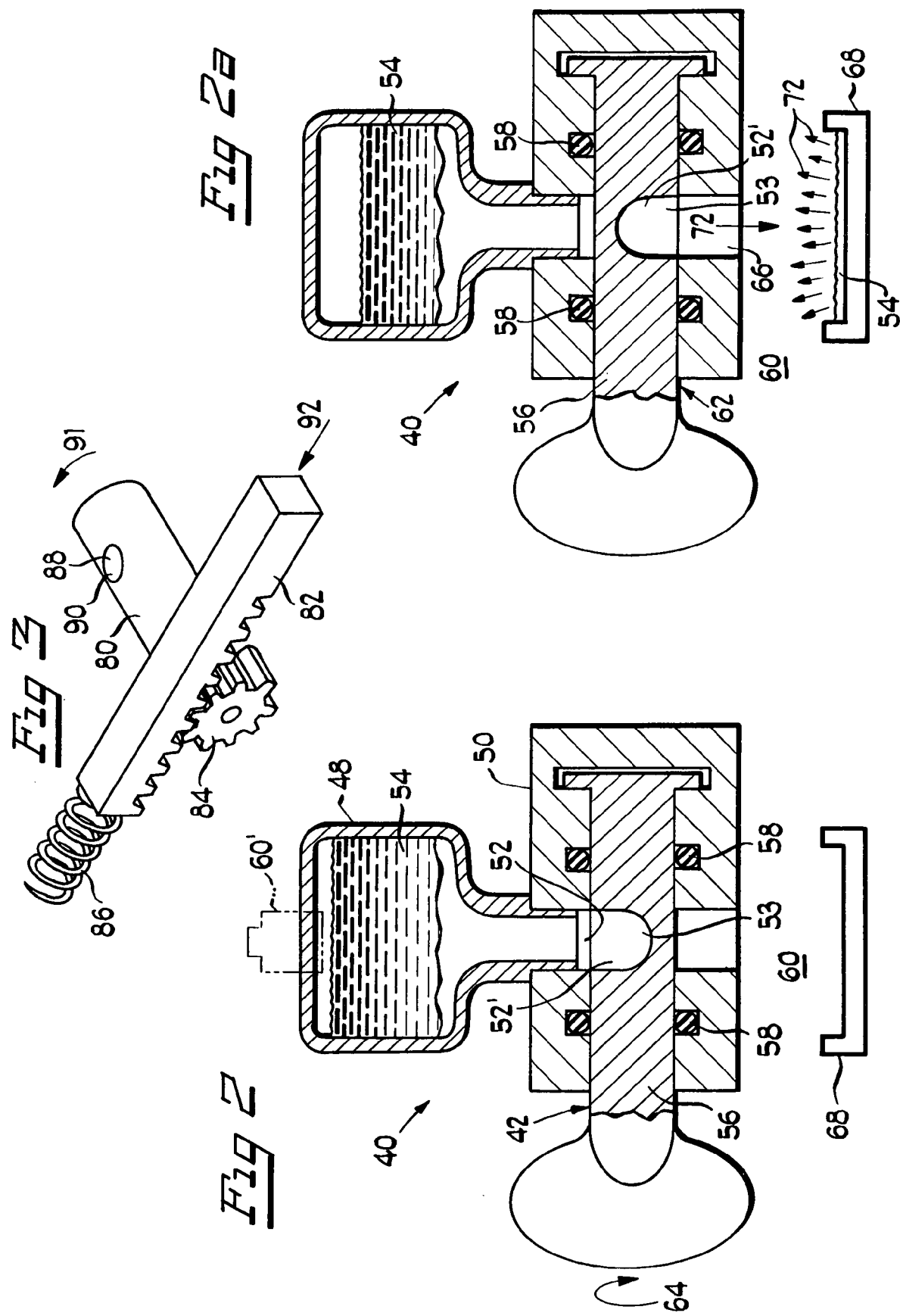

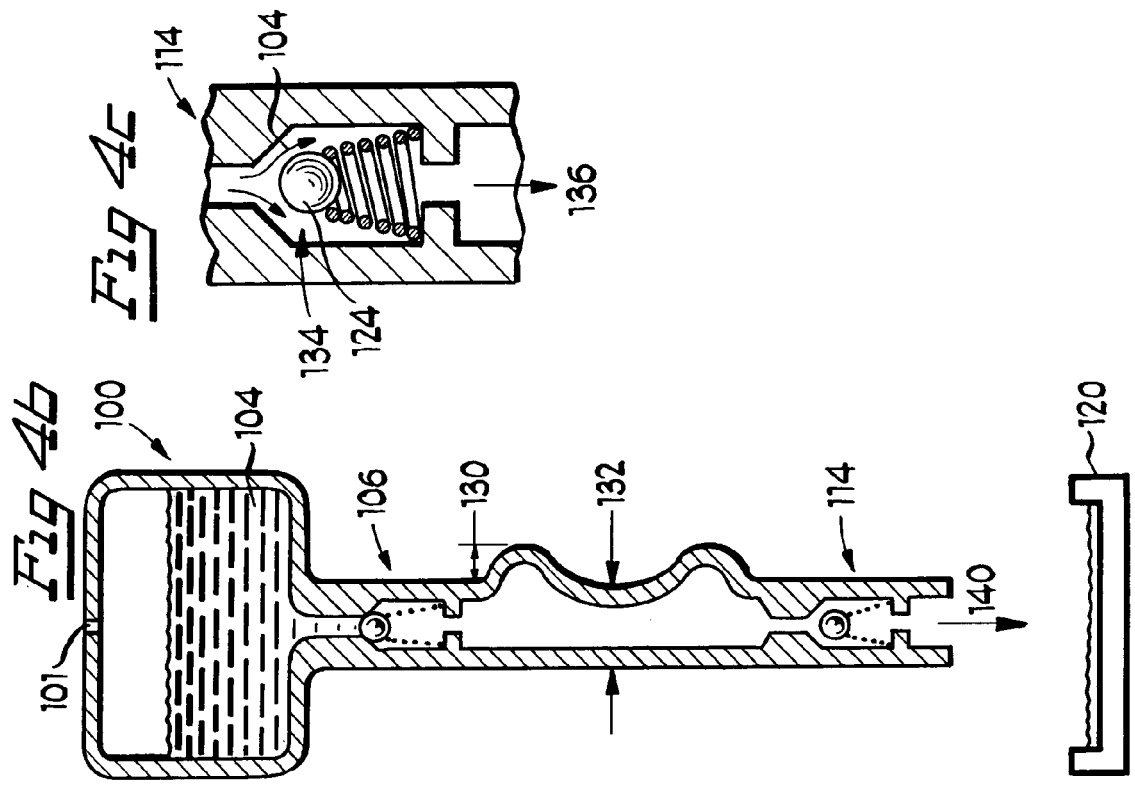
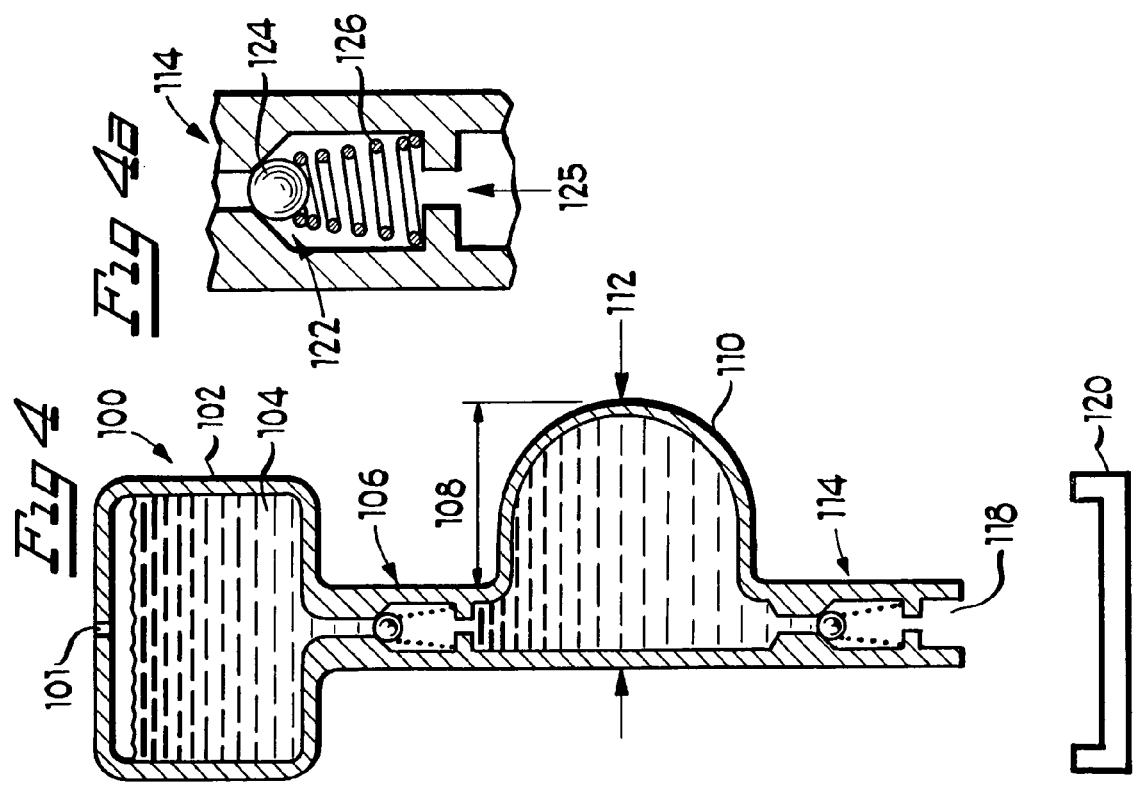

CONTROLLABLE RELEASE OF A VOLATILE SUBSTANCE

BACKGROUND OF INVENTION

1. Field of the Invention

The present invention generally relates to controlling the release of a volatile substance, more particularly, to controlling the release of a predetermined amount of a volatile substance of fluid and isolating the container of the volatile substance from the outside environment.

2. Background Art

Prior art methods for delivering volatile substances from a container, for example a volatile substance such as a liquid, make use of absorbent material such as wicks. For example, one end of a wick is placed in a fluid to be dispensed, while the other end is exposed to the atmosphere. Capillary action will force liquid through the wick and to the exposed end of the wick. Once at the exposed end of the wick the liquid evaporates off of the end of the wick and into the surrounding atmosphere.

Other prior art fluid delivery systems have relied upon various types of gravity driven mechanisms, allowing fluids to diffuse through a membrane under the force of gravity. For instance, Zembrodt, U.S. Pat. No. 4,948,047 shows a container for holding a liquid reservoir which is in contact with a membrane positioned in the bottom of the container. Under the force of gravity, the liquid diffuses through the membrane and volatilizes into the surrounding atmosphere from the exposed surface of the membrane. Likewise, Munteanu, U.S. Pat. No. 4,917,301, discloses a similar container for housing a liquid, with a membrane in the bottom of the container. Gravity again forces the liquid to diffuse through the membrane, from where it then evaporates into the surrounding atmosphere. Joshi et al. also describes gravity based devices in U.S. Pat. Nos. 5,932,204, 6,109,539 and 6,419,163 B1.

Although these and other conventional controlled delivery systems have worked well they have failed to provide for both the controlled fixed amount of fluid to be released while isolating the rest of the fluid under large temperature swings or pressure swings occurring in some applications such as automobiles or airplanes and other temperature and pressure swing environments. Accordingly, such prior art devices have traditionally failed to isolate the volatile fluids from emanating under such high temperature or pressure swings, which, in turn, result in an excessive and rapid volatilization of fluids at a faster rate when no one is occupying the particular environment.

Furthermore such devices have failed to provide a means for a user to selectively dispense only a fixed amount of fluid on the emanator and isolate the rest of fluid in the container from exposure to the atmosphere when the volatile substance needs to be protected from coming into contact with the atmosphere.

SUMMARY OF INVENTION

The present invention comprises a device for controllably releasing a fixed, predetermined amount of volatile substances ("fluid") from a housing and isolating the rest of the fluid from the outside environment. The controlled substance release device comprises a housing, a volatile substance cartridge (for releasably holding a volatile fluid), and means for controllably releasing the substance from the housing on to an emanator pad. The housing further consists of an interior region, a release mechanism in the bottom end of the device, and means for orienting the device so that the force of gravity maintains the volatile substance over the releasing mechanism on the bottom end of the device.

In one preferred embodiment, the device further includes a valve which functions as the controlled release means. The valve is positioned within the opening in the bottom of the device, and is in contact with the volatile substance. At the same time, at least a portion of the bottom surface of the valve is exposed to the atmosphere to allow the fixed amount of volatile substance to dispense from the valve on to an emanator pad. In addition, the device may further comprise means to re-supply the housing with additional amounts of volatile substance. Such re-supplying means may consist of an independent top end to the device, or an inlet port through which the volatile substance may be poured. Moreover, it is also contemplated that the volatile substance may be contained in a replaceable cartridge having means to cooperate with the housing during use of the device, to, in turn, allow the volatile substance to be released from the cartridge.

In another preferred embodiment, the device further comprises a valve, and the housing is constructed of a material which is substantially permeable to ambient air, yet substantially impermeable to the volatile substance contained within the housing—in combination functioning as the controlled release means. The housing may consist of a series of microscopic pores, and may be fabricated from polypropylene, high density polyethylene, and polyethylene, to name a few. The housing allows ambient air to enter the interior region of the housing, thus allowing the volatile substance to dispense through an "on/off" valve when the valve is activated. At the same time, the housing prevents any loss of the volatile substance from the housing walls, through, for instance, a vent, thus preventing uncontrolled loss of the volatile substance, until such time that the valve is activated to dispense a fixed amount of fluid on to the associated emanator. It is likewise contemplated that the housing is substantially flexible yet substantially impermeable to the volatile substance. Once the valve is activated, the fixed amount of volatile substance is dispensed on to an emanator and the rest of the fluid is isolated from coming into contact with the emanator.

In yet another preferred embodiment, the device further comprises a housing with an electrochemical gas generating cell as well as a fixed amount dispensing valve which acts to control the amount of the volatile substance from the housing. The cell emits gases into the interior region of the housing, thus allowing the release of the volatile substance through a valve and onto the emanator and, in turn, into the surrounding atmosphere.

In another preferred embodiment, the device further comprises a dispensing valve in the housing, which is positioned below the volatile substance, and an emanator pad, which is positioned below the valve—thus comprising the controlled release means in this embodiment. The volatile substance drips through the valve when activated, where it falls onto the emanator pad. The emanator pad, in turn retains or absorbs the volatile substance, before the substance volatilizes from the surface of the emanator pad into the surrounding atmosphere.

In still another preferred embodiment, the device further consists of a heating element associated with an emanator which serves to increase the evaporation rate, and thus the release rate of the volatile substance into the atmosphere.

BRIEF DESCRIPTION OF DRAWINGS

FIG. 2 is a side cross sectional view of another embodiment of the controllable release device of the present invention in a pre-release, ready orientation;

FIG. 2a is a side cross sectional view of the controllable release device of FIG. 2, in a fluid dispensing orientation;

FIG. 3 is a perspective view of a sub-assembly of a rack and pinion rotating a pin to activate a controllable release device of one embodiment of the present invention;

FIG. 4 is a side cross sectional view of another preferred embodiment of a controllable release device of the present invention in a pre-release, ready orientation;

FIG. 4a is a sectional view of a check valve shown in FIG. 4 and taken along lines 1—1;

FIG. 4b is a side cross sectional view of the controllable release device of FIG. 4 in a fluid dispensing orientation; and FIG. 4c is a sectional view of a check valve shown in FIG. 4b.

DETAILED DESCRIPTION

The following detailed description is of the best currently contemplated mode of carrying out the invention. The description is not to be taken in a limiting sense, but is made merely for the purpose of illustrating the general principles of the invention, since the scope of the invention is best defined by the appended claims.

Figure 1:
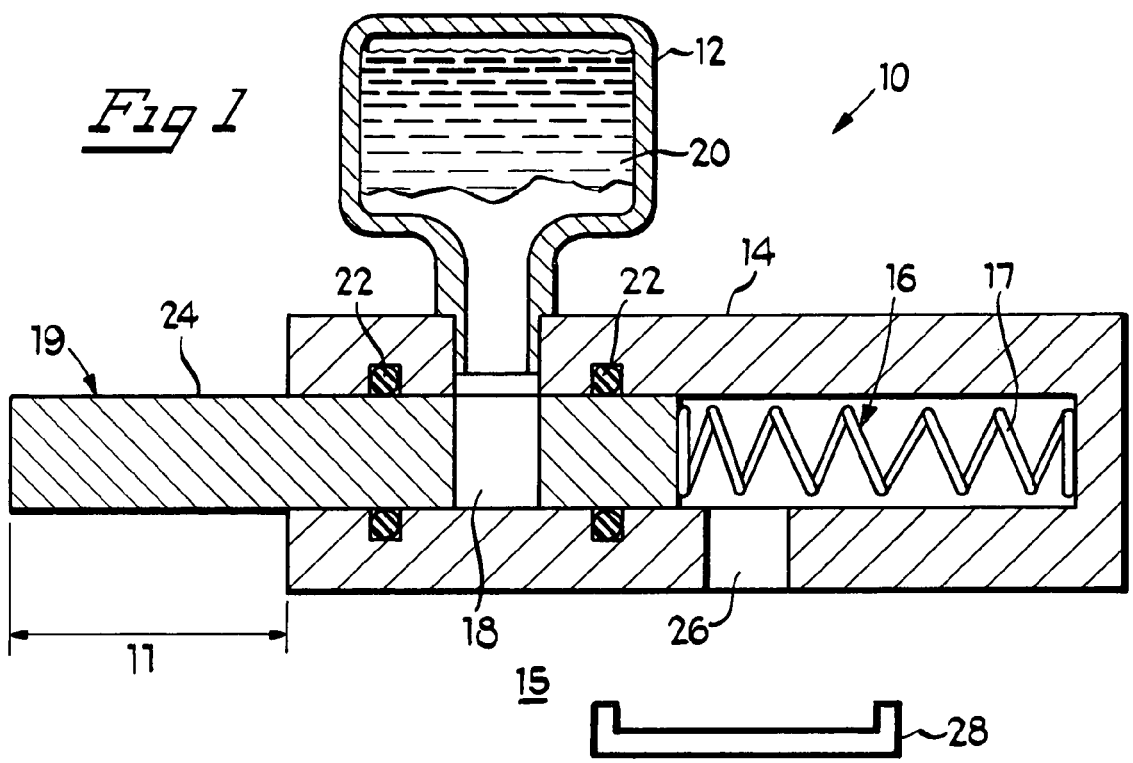
FIG. 1 is a side cross sectional view of the controllable release device of the present invention in a pre-release, ready orientation.

Referring now to FIG. 1 of the drawings, shown is a drawing of a sectional side view of one embodiment of the present invention providing controlled release device 10. Controlled release device 10 is in a ready position 11 and the controlled release device 10 has a fragrance or fluid bottle 12 and a housing 14. The fragrance or fluid bottle 12 may be disposable or may be reusable.

Figure 1A:
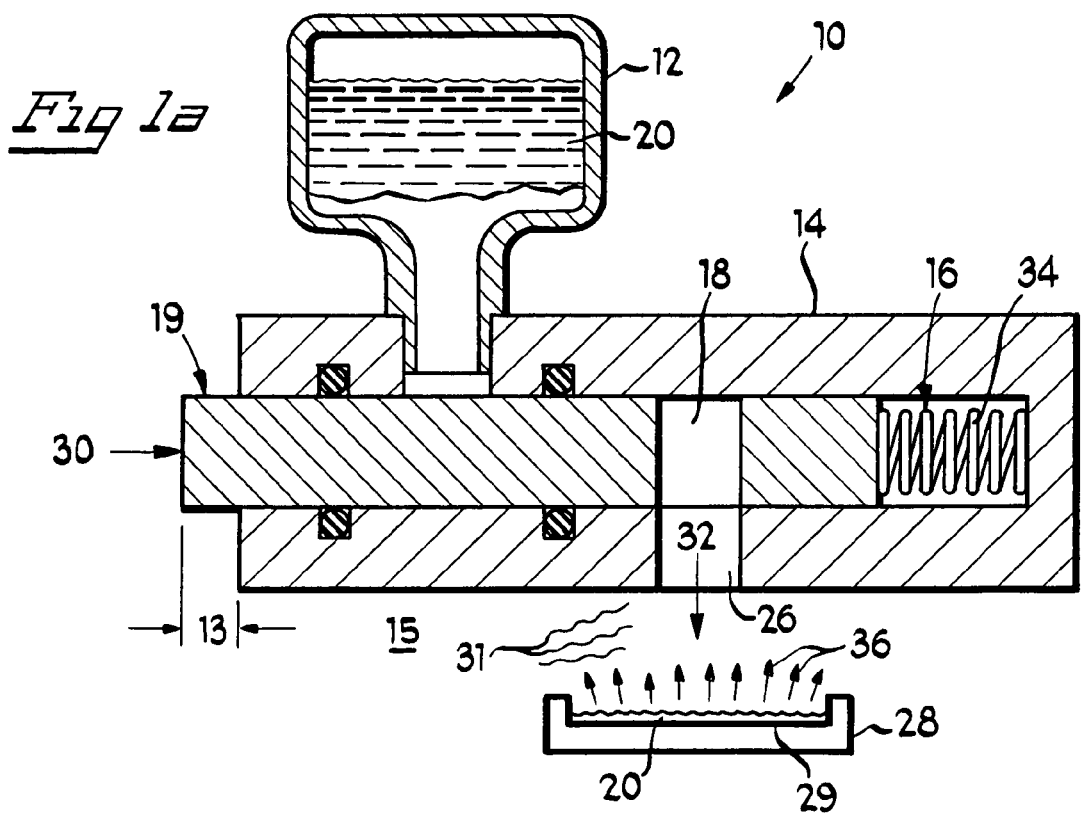
FIG. 1a is a side cross sectional view of the controllable release device shown in FIG. 1, in a fluid dispensing orientation.

In FIG. 1, as in one embodiment of the present invention, device 10 includes spring 16 and chamber 18 disposed inside housing 14. Volatile substance, or fluid, 20 is inside fluid bottle/cartridge 12 when a shuttle 24 is in the ready position 11. When shuttle 24 is in the ready or dispensing position 13 (FIG. 1a), seals 22 protect fluid 20 from the outside environment or atmosphere 15 by closing off the environment or atmosphere 15 from fluid 20. Seals 22 close off atmosphere 15 by providing contact with shuttle 24 and housing 14. Shuttle 24 is positioned in the ready position 11 and dispensing position 13 by spring 16 which is in contact with shuttle 24. Spring 16 provides the ready position 11 when in a substantially uncompressed state 17. Conversely, spring 16 provides the dispensing position 13 when in a substantially compressed state 34 (FIG. 1a). Controller 19 provides the force 30 and timing to compress spring 16. As will be understood, the controller may comprise mechanical actuation by a user, or, an electromechanical switch for activation. Other conventional controlling/activating means are likewise contemplated for use.

Referring to FIG. 1a, as in one embodiment of the present invention, shown is controlled release device 10 in dispensing position 13 with spring 16 in a substantially compressed state. Force 30 causes chamber 18 to line up with discharge hole 26. Emanator 28 is provided under the discharge hole 26. When chamber 18 lines up with discharge hole 26, fluid 20 is allowed to exit 32 housing 14 and collect on emanator 28. Vapors 36 leave fragrance 20 and fill the environment or atmosphere 15. Emanator 28 has an emanator surface 29.

Controlled release device 10 can be activated by control 19 to fill the environment or atmosphere 15 with fluid 20 (such as a volatile fragrant fluid) for a certain period of time, and may be activated manually when more fragrance or fluid 20 is desired. For example, in a cabin of an automobile, the controller 19 may be a driver who can place controlled release device 10 in dispensing position 13 when, for example, the driver first enters the automobile. The driver may move shuttle 24 into dispensing position 13 once, or a multiple of times as desired. Fragrance or fluid 20 will be in the environment or atmosphere 15 for a period of time and may be boosted with a second, or subsequent activations by pushing the controller 19 when desired.

Again, as shown in FIG. 1a, emanator surface 29 can be an absorbent pad or a simple hard surface, amongst others. Also the emanator surface can be heated to promote fragrance or fluid evaporation 31. Further emanator surface 29 may be placed in the airflow of a fan or a car vent or other such acceleration and distribution means.

Referring to FIG. 2, according to another embodiment of the present invention, shown are drawings of one embodiment of the present invention providing controlled release device 40. Controlled release device 40 is shown in the ready position 42. Also shown is a fragrance or fluid bottle/cartridge 48 and a housing 50. The fragrance or fluid bottle/cartridge 48 may be disposable or may be reusable. When the bottle is disposable, it is contemplated that a replacement bottle/cartridge (filled with fluid) be substituted in its place. Release and replacement of the cartridge can be accomplished by any number of conventional means such as threaded releasable securement to the housing, snap-fit, biasing means, ratched mechanisms, etc. Alternatively, the cartridge may include a sealable aperture for enabling re-filling with additional fluid.

Chamber 52 is disposed inside housing 50. A dosage 53 of fluid 54 is released from cartridge 48 and into chamber 52, which is formed in a cup-like shape in rotating pin 56. Rotating pin 56 is shown in the ready position 42, in FIG. 2, when cup-like chamber 52 aligns with opening 52' of cartridge 48. When rotating pin 56 is in the ready position 42, seals 58 protect fragrance/fluid 54 from an outside environment or atmosphere 60 by closing off the environment or atmosphere 60 from fragrance 54. Seals 58 close off atmosphere 60 by providing contact with the rotating pin 56 and housing 50. Rotating pin 56 is positioned in the ready position 42 and dispensing position 62 (see FIG. 2a) by controller 64. Controller 64 provides the ready position 42 and may be rotated 180 degrees (with mechanical stops, if desired) thereby moving to dispensing position 62. Also, controller 64 may provide the ready position 42 and dispensing position 62 by using a spring return mechanism, among other types of return means. Also shown in FIG. 2 is optional gas generating cell 60' which can assist in gravitational displacement of fluid.

Controlled release device 40 is shown in FIG. 2a in a dispensing position 46. As can be seen, chamber 52 is lined up with discharge hole 66 of housing 50. Dosage 53 passes from chamber 52 through discharge hole 66 to emanator 68. Emanator 68 is provided under discharge hole 66. When chamber 52 lines up with discharge hole 66, fragrance 20 is allowed to exit 72 housing 50 and collect on emanator 68. Vapors 76 leave fragrance 54 and fill the environment or atmosphere 60.

Referring to FIG. 3, shown is another preferred embodiment of a rotating mechanism which can be used in the present invention. The rotating mechanism includes rotating pin 80 by way of a rack 82 and pinion 84. Further shown is return spring 86 and fragrance dose chamber 88. Rotating pin 80 rotates 91 to dump a dosage 90 when the rack 82 is pushed 92.

Referring to FIG. 4, according to another embodiment of the present invention, shown is controlled release device 100. Furthermore, as can be seen, the controlled release device is in a ready potion 108. Fluid reservoir 102, with fluid 104 inside includes vent 101. A dispensing chamber inlet valve 106 is below the fluid reservoir 102. The ready position 108 provides a dispensing chamber or bubble 110 filled with fluid 104. Dispensing chamber 110 is generally made of a flexible material. Activation force 112 is placed on the dispensing chamber 110.

Discharge valve 114 is positioned below dispensing chamber 110 and above fluid outlet 118. Emanator 120 is positioned below the fluid outlet. Both the dispensing chamber inlet check valve 106 and the discharge valve 114 may be one-way check valves. Referring to FIG. 4a, shown is an exploded cross sectional view of the discharge valve 114. Discharge valve 114 is in a closed state 122 with ball 124 providing a seal force 125 from an un-compressed spring 126.

Referring to FIG. 4b as in one embodiment of the present invention, provided is controlled release device 100 in a dispensing position 130. Dispensing chamber inlet check valve 106 is closed and discharge valve 114 is open. Dispensing chamber 110 is collapsed 132 by activation force (squeezing) causing fluid 104 to be forced out discharge valve 114 and onto emanator or evaporation surface 120. Referring to FIG. 4c is an exploded cross sectional view of the discharge valve 114. Discharge valve 114 is in an open state 134 with ball 124 allowing fluid 104 to pass with a compressed spring 136.

As can be seen in FIGS. 4 and 4b, a means for providing a predetermined dose 140 by using a flexible bubble or dispensing chamber 110 and two-one way check valves 106 and 114 is disclosed. With dispensing chamber 110 full, compression forces are applied and fluid 104 is forced through the discharge valve 114 and the outlet 118 and onto the emanator 120. When the dispensing chamber 110 is compressed, the inlet valve or dispensing chamber inlet valve 106 is forced closed to prevent fluid 104 from moving back into the fluid reservoir 102.

When dispensing chamber 110 is released, bubble 110 expands back toward its original shape prior to the application of the compression forces. At this time the outlet valve 114 is shut preventing air from being sucked into bubble 110. As bubble 110 expands it draws fluid in through inlet valve 106 from reservoir 102 so that bubble 110 is full and ready for another dose 140. As fluid 104 moves from the reservoir 102 into bubble 110, the volume of the reservoir 102 is replaced by air entering vent 101.

It should be understood, of course, that the foregoing relates to preferred embodiments of the invention and that modifications may be made without departing from the spirit and scope of the invention as set forth in the following claims.

The invention claimed is:

1. A device for releasing a volatile substance into an environment comprising:

a housing having an interior region, an outer surface, and an discharge opening, wherein the housing includes a volatile substance cartridge having an outlet for containing a volatile substance therewithin;

means for orienting the device such that gravity forces the volatile substance toward the outlet of the cartridge and into a chamber configured to temporarily retain the volatile substance; and means for moving the chamber such that an opening in the chamber is in communication with the discharge opening such that a fixed amount of the volatile substance dispenses onto an emanator, and wherein the volatile substance in the cartridge of the housing is substantially protected from exposure to the outside environment, said chamber being movable into a position for receiving volatile substance from the outlet will preventing said volatile substance from dispensing onto the emanator.

2. A device for releasing a volatile substance into an environment comprising:

a housing having an interior region, an outer surface, and an discharge opening, wherein the housing includes a volatile substance cartridge for containing a fluid therewithin, the cartridge having an outlet;

a chamber for temporarily holding the volatile substance the chamber having a first opening for receiving volatile substance from the cartridge outlet; and a controller for moving the chamber such that a second opening in the chamber is in communication with the discharge opening such that a fixed amount of the volatile substance dispenses onto an emanator, the controller being movable into a position for receiving volatile substance from the outlet will preventing said volatile substance from dispensing onto the emanator.

3. The device of claim 2, wherein the housing and the controller isolate the volatile substance from the outside air and substantially prevent loss of the volatile substance until and after a desired release.

4. The device of claim 2, wherein the housing, controller and emanator can operate with large swings in temperature and pressure of the outside environment.

5. The device according to claim 2, wherein the controller further comprises a rotatable valve for releasing a fixed amount of volatile substance onto an emanator to be released over time into the surrounding environment.

6. The device according to claim 2, further including seals for protecting volatile substance in the cartridge from exposure to the outside environment.

7. The device according to claim 2, wherein the controller comprises an electrically operated valve which releases fixed amounts of the volatile substance onto the emanator while isolating the remaining volatile substance in the housing from the outside environment such that there is substantially no loss of volatile substance until the chamber is moved.

8. The device according to claim 2, wherein the device is configured for use in automobiles, vehicles, airplanes, trains or other room spaces where large temperature and pressure swings exist.

9. The device according to claim 2, wherein the emanator is selected from the group consisting of porous plastic, cellulose pads, porous glass, ceramic pads, heated pads, piezo electric pads or ultrasonic pads, fans and combinations thereof.

10. The device according to claim 2, wherein the housing is constructed of a substantially rigid material having means for allowing air to fill the space when a predetermined amount of volatile substance controllably leaves the reservoir.

11. The device according to claim 2, wherein the volatile substance is selected from the group comprising fragrances, medicaments, insect repellants, cleaning chemicals and combination thereof.

12. The device according to claim 2, wherein the controller comprises a frame with a shuttle inside, the shuttle defining the chamber, the controller further comprising a plurality of seals surrounding the shuttle, and a biasing spring in contact with the shuttle.

13. The device according to claim 2, wherein the first and second opening of the chamber are the same opening.

14. The device according to claim 2, wherein the controller comprises a rotating pin.

15. The device according to claim 14, wherein the rotating pin includes mechanical stops.

16. The device according to claim 14, wherein the rotating pin has a spring return.

17. The device according to claim 2, wherein the emanator further comprises a surface to receive the fluid, the surface being an absorbent pad.

18. The device according to claim 2, wherein the emanator further comprises a surface to receive the fluid, the surface being a hard surface.

19. The device according to claim 2, further comprising a heating element in communication with the emanator for increasing volatilization.

20. The device according to claim 2, further comprising means for increasing airflow adjacent the emanator.

21. The device according to claim 2, wherein the cartridge is replaceable.

22. The device according to claim 2, wherein the cartridge is refillable.

23. A method of releasing a volatile substance into an outside environment comprising the steps of:

storing a volatile substance in a reservoir;

releasing a fixed dose of the volatile substance from the reservoir into a chamber;

temporarily holding the volatile substance in the chamber;

moving the chamber by actuating a controller such that the volatile substance exits the chamber onto an emanator; and vaporizing the fixed dose of the volatile substance into the outside.

24. The method of claim 23, wherein the step of releasing volatile substance into a chamber comprises the step of activating the controller from a first position to a second position while preventing release of the volatile substance onto the emanator.

25. The method of claim 23, wherein the step of moving the chamber is selected from the steps of manually or electronically moving the chamber.

* * * * *